US00PP20447P3

(12) United States Plant Patent
Pierron-Darbonne

(10) Patent No.: US PP20,447 P3
(45) Date of Patent: Nov. 3, 2009

(54) STRAWBERRY PLANT NAMED 'CRISTAL'

(50) Latin Name: ***Fragaria ×ananassa* DUCH**
Varietal Denomination: CRISTAL

(75) Inventor: Alexandre Pierron-Darbonne, Le Barp (FR)

(73) Assignee: Plantas De Navarra, S.A. (ES)

( * ) Notice: Subject to any disclaimer, the term of this patent is extended or adjusted under 35 U.S.C. 154(b) by 0 days.

(21) Appl. No.: 12/156,730

(22) Filed: Jun. 3, 2008

(65) Prior Publication Data

US 2008/0320626 P1 Dec. 25, 2008

(30) Foreign Application Priority Data

Jun. 6, 2007 (EP) ..... 2007/1257

(51) Int. Cl.
*A01H 5/00* (2006.01)

(52) U.S. Cl. ..... Plt./208

(58) Field of Classification Search ..... Plt./208
See application file for complete search history.

*Primary Examiner*—Annette H Para
(74) *Attorney, Agent, or Firm*—Christie, Parker & Hale, LLP.

(57) ABSTRACT

The present invention relates to a new and distinct strawberry variety. The varietal denomination of the new variety is 'Cristal'. Among the characteristics which appear to distinguish the new variety from other varieties are a combination of traits which include inflorescence that appears above the foliage same size of calyx relative to corolla and abundant production of dark red colored, almost cylindrical shaped, and firm fruit, large fruit size, and early time of ripening.

8 Drawing Sheets

Figure 1:
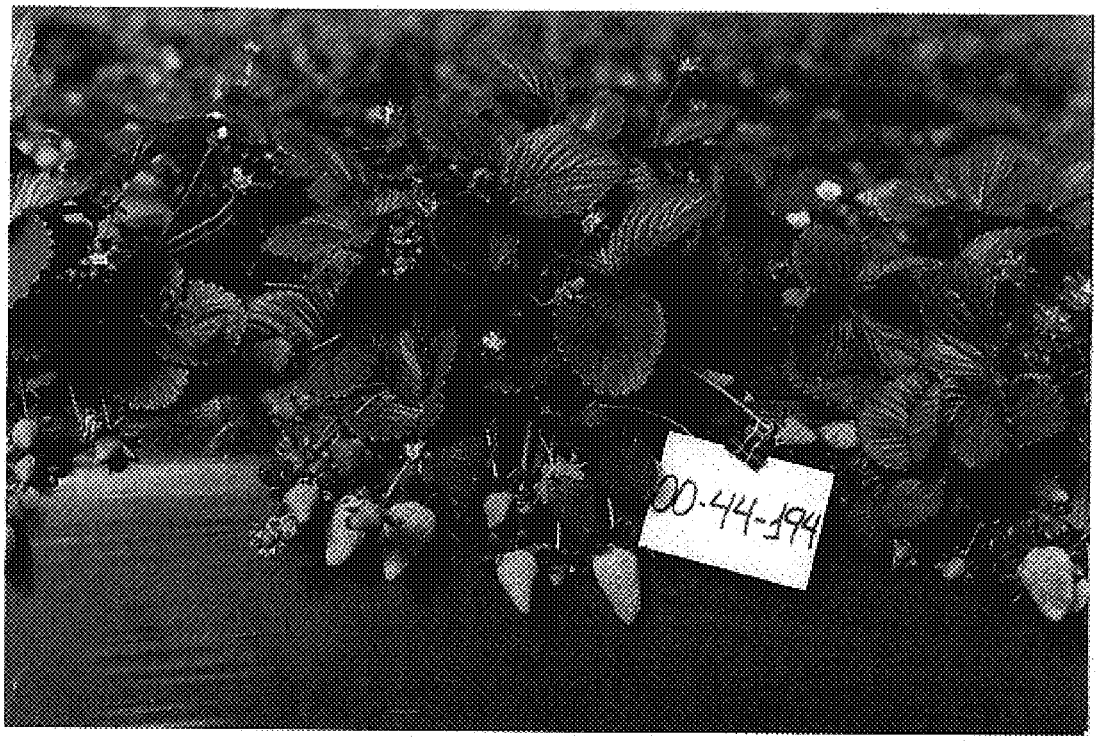

Botanical classification: *Fragaria×ananassa* Duch.

Varietal denomination: The new plant has the varietal denomination 'Cristal'.

BACKGROUND OF THE INVENTION

The new variety of strawberry was created in a breeding program by crossing two parents; in particular, by crossing as seed parent an undistributed strawberry parent designated 9261 (unpatented) and as pollen parent an undistributed strawberry parent designated 9045 (unpatented). Female and male are selections from breeder's program of Planasa. Both parental varieties are property and have not been commercialized.

The resulting seedling of the new variety was grown and asexually propagated by runners in Segovia, Spain, 3° 59'W., 41° 22'N., 2742 feet elevation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Cristal'. Among the characteristics which appear to distinguish the new variety from other varieties are a combination of traits which include inflorescence that appears above the foliage, same size of calyx relative to corolla and abundant production of dark red colored, almost cylindrical shaped, and firm fruit, large fruit size, and early time of ripening (50% of plants with ripe fruits).

COMPARISON TO CLOSEST VARIETY

The new variety is closest to the variety 'Aires' (U.S. Plant Pat. No. 9,757), but is distinguished therefrom by the following characteristics possessed by 'Cristal' which are different than, or not possessed by, 'Aires' (U.S. Plant Pat. No. 9,757).

1. 'Aires' (U.S. Plant Pat. No. 9,757) exhibit a plant more dense than 'Cristal'.
2. 'Aires' (U.S. Plant Pat. No. 9,757) shows a leaf color of upper side (RHS green group near 135 B to 135 A) more dark than 'Cristal' (RHS green group near 141 B to 141 A).
3. Shape in cross section of the leaf in 'Aires' (U.S. Plant Pat. No. 9,757) is flat to slightly convex, than in 'Cristal' it is slightly concave.
4. Glossiness of the leaf in 'Aires' (U.S. Plant Pat. No. 9,757) is less strong than in 'Cristal'.
5. In 'Aires' (U.S. Plant Pat. No. 9,757) the position of the inflorescence relative to foliage is beneath, in 'Cristal' it is above.
6. Size of calyx relative to corolla of the flower in 'Aires' (U.S. Plant Pat. No. 9,757) is smaller and the relative position of petals is touching, than in 'Cristal' the size of calyx relative to corolla is same size and the relative position of petals is overlapping.
7. The fruit shape of 'Aires' (U.S. Plant Pat. No. 9,757) is conical whereas in 'Cristal' is almost cylindrical.
8. 'Aires' (U.S. Plant Pat. No. 9,757) shows a red fruit color (RHS red group near 44 A to 42 A), whereas in 'Cristal' it is an dark red fruit color (RHS red group near 46 B to 45 A).
9. Band without achenes in fruit of 'Aires' (U.S. Plant Pat. No. 9,757) is absent or very narrow whereas in the fruit of 'Cristal' is narrow.
10. The glossiness of fruit in 'Aires' (U.S. Plant Pat. No. 9,757) is medium whereas in the fruit of 'Cristal' is strong.

The differences in the leaf color of upper side of 'Cristal' (designated 00.44.194) and 'Aires' (U.S. Plant Pat. No.

Figure 3:
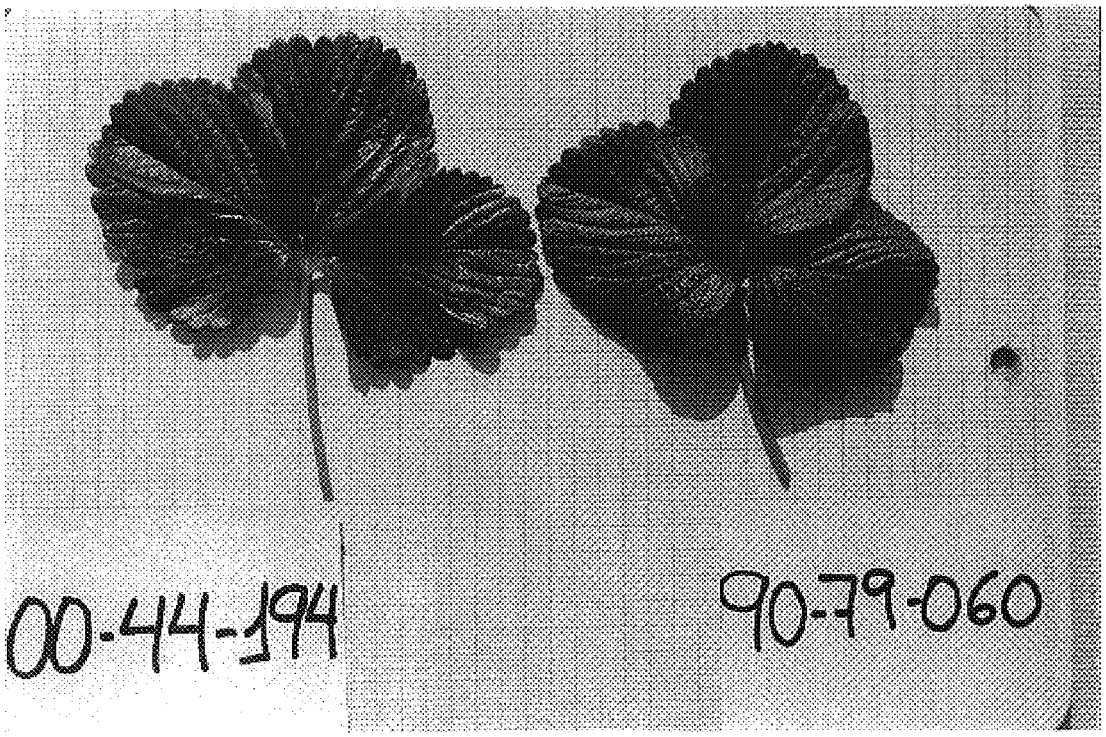
Figure 6:
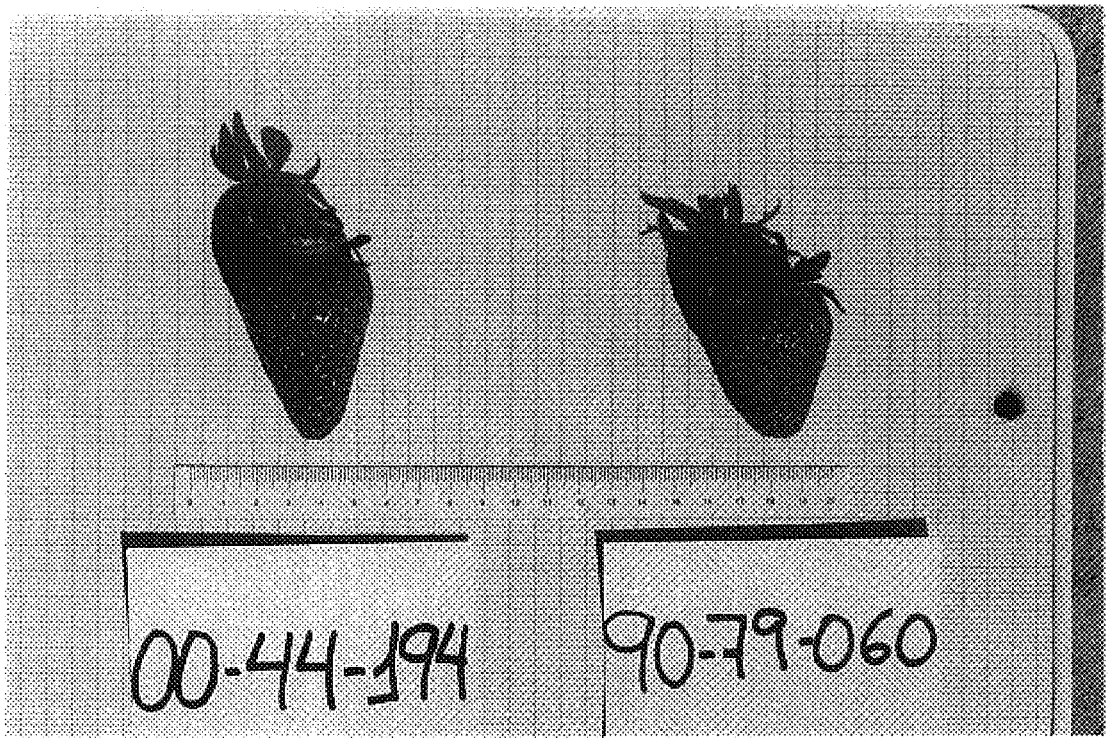

9,757) (designated 90.79.060) are shown in FIG. 3. The differences in the fruits of 'Cristal' and 'Aires' (U.S. Plant Pat. No. 9,757) are shown in FIG. 6. These differences are maintained during the harvest season.

11. 'Cristal' shows a firmness fruit slightly more than 'Aires' (U.S. Plant Pat. No. 9,757).
12. Time of ripening in 'Aires' (U.S. Plant Pat. No. 9,757) is very early whereas in 'Cristal' is early.

BRIEF DESCRIPTION OF ILLUSTRATIONS

The accompanying photographs show typical specimens of the new variety, designated 00.44.194 in the illustrations, including fruit, foliage and flower, in color as nearly true as it is reasonably possible to make in color illustrations of this character.

The plants depicted in the drawings were planted Oct. 15, 2007 in the farm of La Mogalla in Cartaya (Huelva), Spain, about 7° W., 37° N., 45 feet elevation.

Drawings were taken April, 2008 (about Apr. 15, 2008): minimum temperate about 10 to 12° Centigrade, maximum temperate about 22 to 24° Centigrade.

FIG. 1 shows several plants of the new variety (designated 00.44.194) which exhibit a plant less dense than 'Aires' (U.S. Plant Pat. No. 9,757) (designated 90.79.060). The plants of the new variety (designated 00.44.194) exhibit the position of the inflorescence relative to foliage is above.

Figure 2:
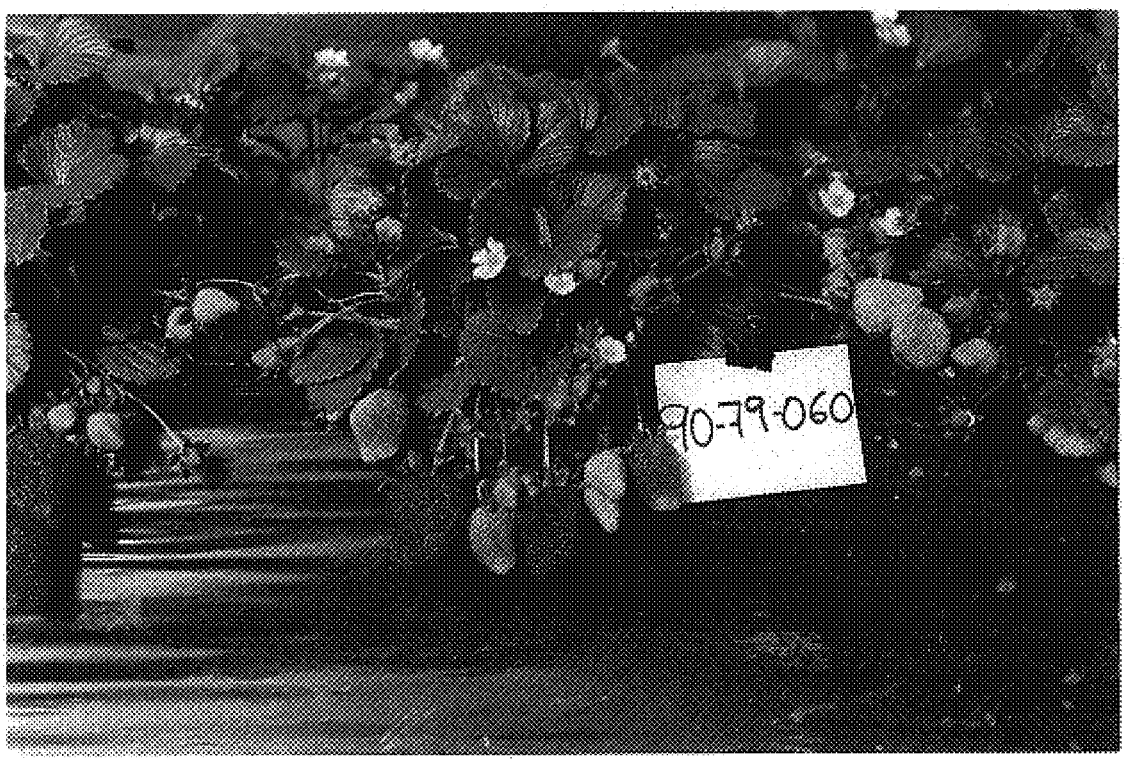

FIG. 2 shows several plants of strawberry variety 'Aires' (U.S. Plant Pat. No. 9,757) (designated 90.79.060) which exhibit a plant more dense than the new variety (designated 00.44.194). The plants of the strawberry variety 'Aires' (U.S. Plant Pat. No. 9,757) (designated 90.79.060) exhibit the position of the inflorescence relative to foliage is beneath.

FIG. 3 shows the top of a complete leave of the new variety (designated 00.44.194) and a complete leave of strawberry variety 'Aires' (U.S. Plant Pat. No. 9,757) (designated 90.79.060). In it we can see that the leaf color of upper side of 'Aires' (U.S. Plant Pat. No. 9,757) (designated 90.79.060) is more dark (RHS green group near 135 B to 135 A) than in the new variety (designated 00.44.194) (RHS green group near 141 B to 141 A). Shape in cross section of the leaf in 'Aires' (U.S. Plant Pat. No. 9,757) (designated 90.79.060) is flat to slightly convex, than in the new variety (designated 00.44.194) it is slightly concave. Glossiness of the leaf in 'Aires' (U.S. Plant Pat. No. 9,757) (designated 90.79.060) is less strong than in the new variety (designated 00.44.194).

Figure 4:
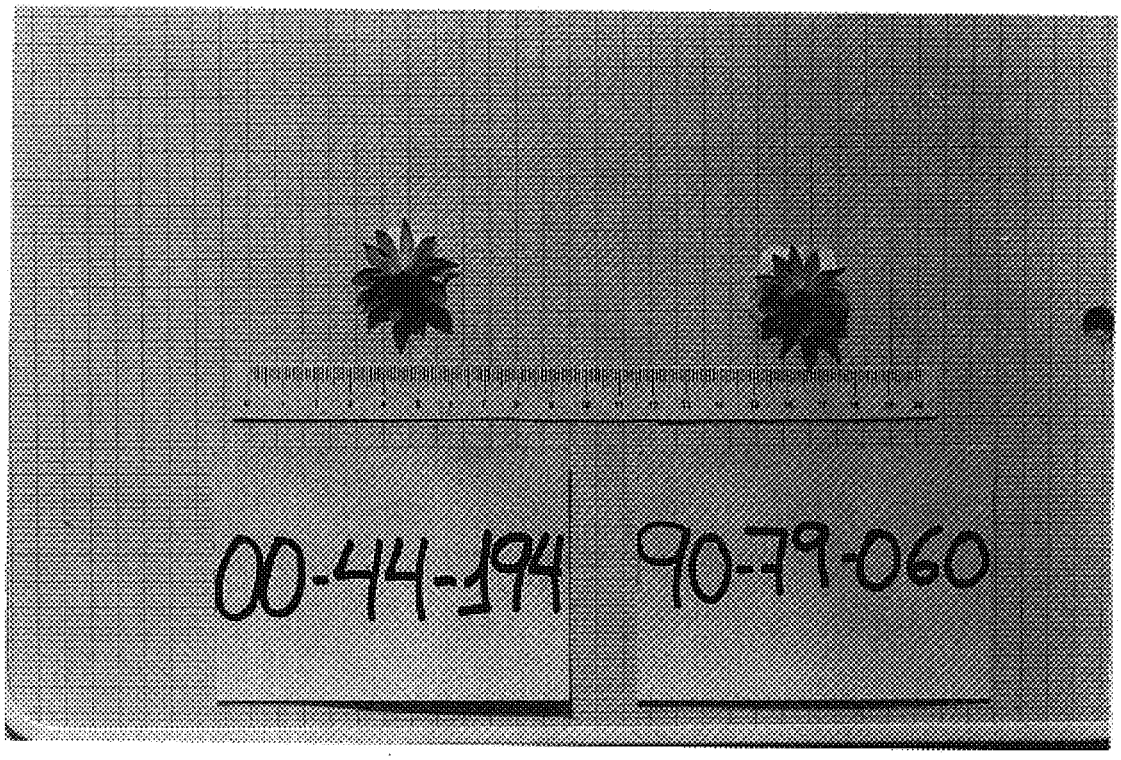
Figure 5:
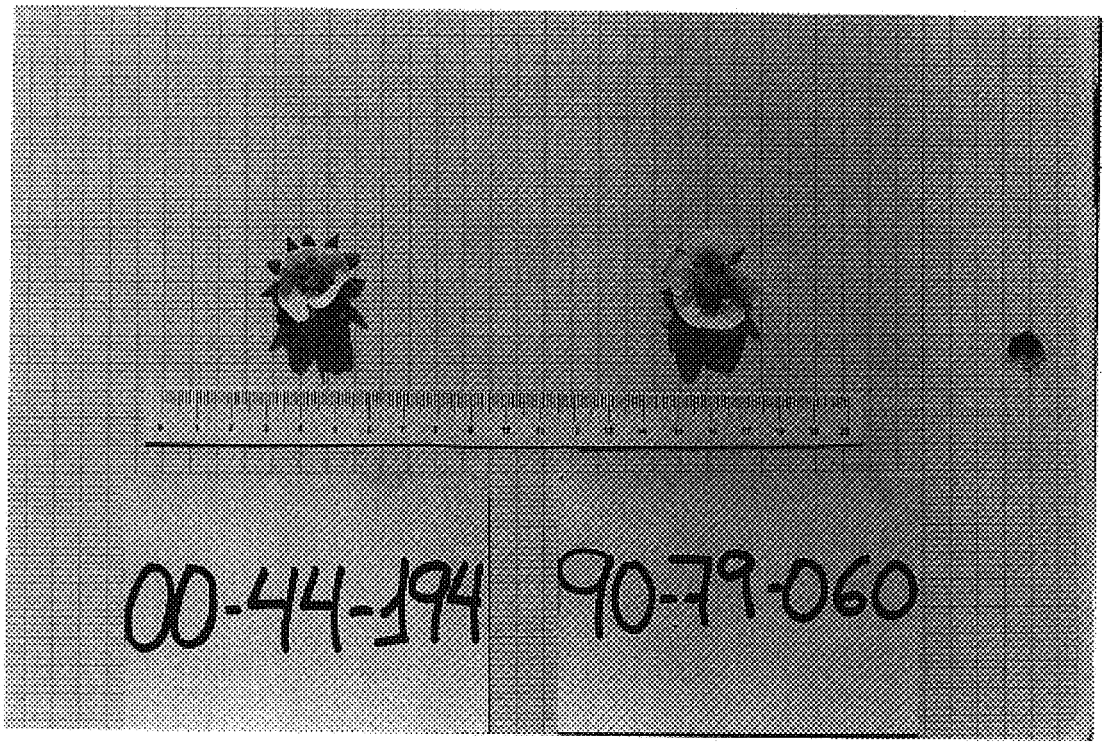

FIG. 4 and FIG. 5 show the flower of the new variety (designated 00.44.194) and the flower of strawberry variety 'Aires' (U.S. Plant Pat. No. 9,757) (designated 90.79.060). In it we can see that the size of calyx relative to corolla of the flower in 'Aires' (U.S. Plant Pat. No. 9,757) (designated 90.79.060) is smaller and the relative position of petals is touching, than in the new variety (designated 00.44.194) the size of calyx relative to corolla is same size and the relative position of petals is overlapping.

FIG. 6 shows the comparison between fruits of the new variety (designated 00.44.194) and the flower of strawberry variety 'Aires' (U.S. Plant Pat. No. 9,757) (designated 90.79.060). In it we can see that the fruit shape of 'Aires' (U.S. Plant Pat. No. 9,757) (designated 90.79.060) is conical whereas in the new variety (designated 00.44.194) is almost cylindrical. Flower and reproductive organs of the new variety (designated 98.08V.134). 'Aires' (U.S. Plant Pat. No. 9,757) (designated 90.79.060) shows a red fruit color (RHS red group near 44 A to 42 A), whereas in the new variety (designated 00.44.194) it is an dark red fruit color (RHS red group near 46 B to 45 A). Band without achenes in fruit of 'Aires' (U.S. Plant Pat. No. 9,757) (designated 90.79.060) is absent or very narrow whereas in the fruit of the new variety (designated 00.44.194) is narrow. The glossiness of fruit in 'Aires' (U.S. Plant Pat. No. 9,757) (designated 90.79.060) is medium whereas in the fruit of the new variety (designated 00.44.194) is strong.

Figure 7:
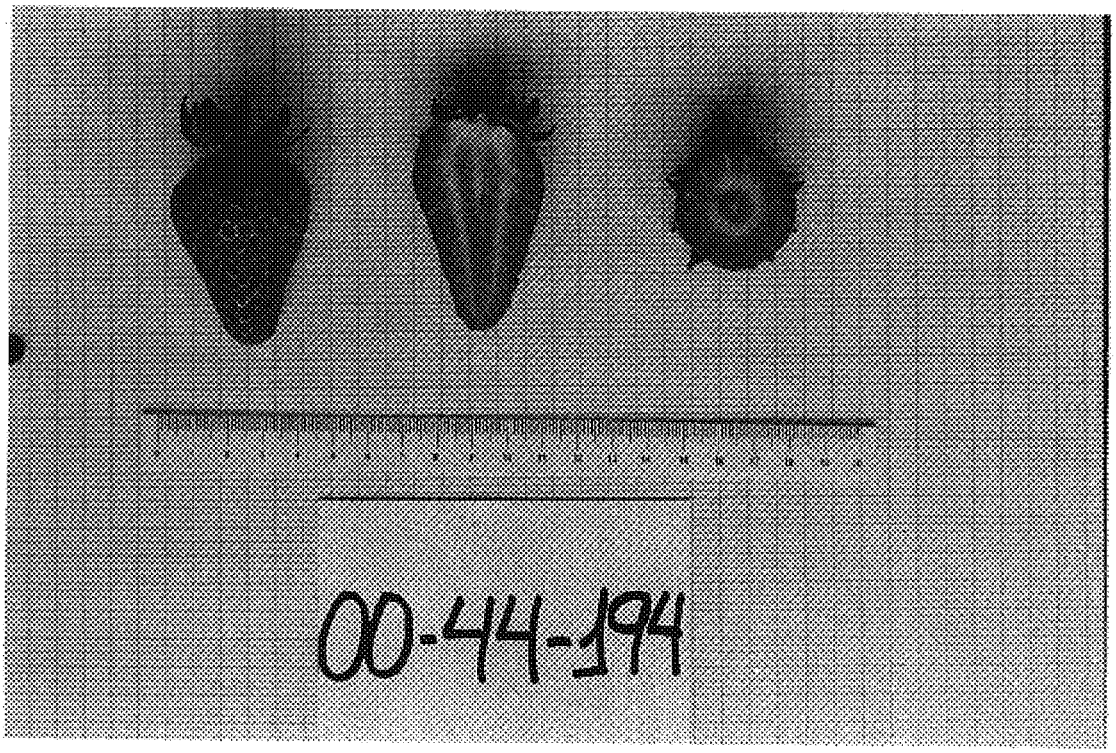
Figure 8:
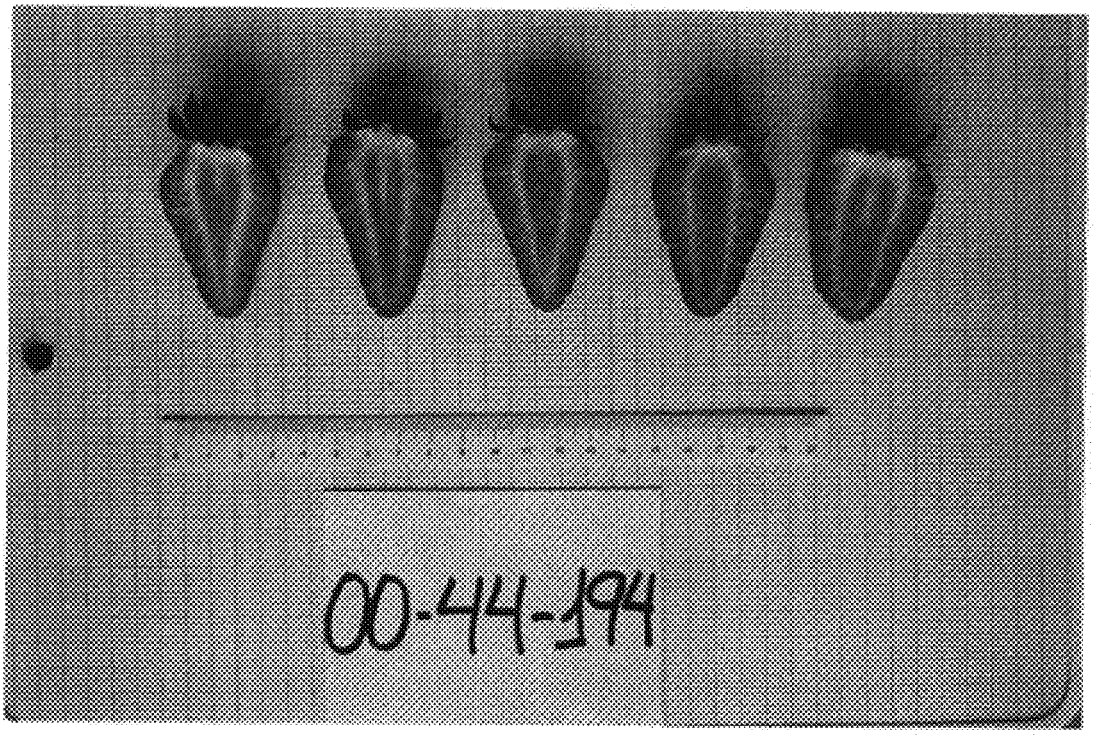

FIGS. 7 and 8 show typical fruit of the new variety (designated 00.44.194) whole, sliced and in cross section, illustrating the typical flesh and flesh coloration (RHS red group near 43 B to 43 A), conspicuous core and core cavity, almost cylindrical shape and dark red fruit color (RHS red group near 46 B to 45 A).

DESCRIPTION OF THE NEW VARIETY

The following detailed description of the new variety is based upon observations taken of plants and fruits grown "underglass", i.e. undertunnel, in the farm of La Mogalla in Cartaya (Huelva), Spain, 7° W., 37° N., 45 feet elevation.

The following description is in accordance with UPOV terminology and the color terminology herein is in accordance with The Royal Horticultural Society Colour Chart (R.H.S.C.C.). The color descriptions and other phenotypical descriptions may deviate from the stated values and descriptions depending upon variation in environmental, seasonal, climatic and cultural conditions.

PROPOGATION

The new variety is principally propagated by way of runners. Although propagation by runners is presently preferred, other know methods of propagating strawberry plants may be used. Strawberries root well after transplanting.

The term "blistering" used herein refers to the texture or rugosity or surface ondulation inherent to leaves and is generally a constant characteristic.

GENERAL

'Cristal' is a fully remontant (non flowering runners) variety and do not needs an induction to flowering by chilling (fresh plant) or with cold storage (referred to as a frigo). 'Cristal' is self-fertile. It produces large quantity of pollen throughout the seasons and pollination is generally good as there are very few malformed fruit.

*Production.*—Plants described are from high elevation nursery. Trials pursued in Cartaya (Huelva), Spain. Date of planting: 15th Oct. 2007. Number of repetitions: 2. Plants per repetition: 225.

Comparison with 'Aires' (U.S. Plant Pat. No. 9,757). The new variety is compared with 'Aires' (U.S. Plant Pat. No. 9,757) (designated 90.79.060) in FIG. 1 and FIG. 2 and FIG. 3 and FIG. 4 and FIG. 5 and FIG. 6.

| Accumulated production of 1st quality fruit (g/plant) | | | | |
|---|---|---|---|---|
| Variety | 21 February | 28 March | 25 April | 15 May |
| AIRES | 54 | 270 | 520 | 677 |
| CARLSBARD | 108 | 399 | 595 | 708 |
| CRISTAL | 74 | 344 | 791 | 992 |

-continued

| Accumulated production of 1st quality fruit (g/plant) | | | |
|---|---|---|---|
| Variety | 1st + 2nd Quality Fruit | Total | Weight (g/fruit) |
| AIRES | 677 + 129 | 806 | 23-21 |
| CARLSBARD | 708 + 75 | 783 | 25-23 |
| CRISTAL | 992 + 66 | 1058 | 24-22 |

| Production total, to 15 May, of First Quality Fruit (1st quality) and Second Quality Fruit (2nd quality) in g/plant | | | | |
|---|---|---|---|---|
| Variety | 1st quality | 2nd quality | TOTAL (1st quality + 2nd quality) | % 2nd quality |
| AIRES | 677 | 129 | 806 | 16 |
| CARLSBARD | 708 | 75 | 783 | 10 |
| CRISTAL | 992 | 66 | 1058 | 6 |

$$\% \ 2^{nd} \text{ quality} = \frac{2^{nd} \text{ quality}}{\text{TOTAL}} \times 100$$

| Weight (g/Fruit) at two dates: 28 March and 15 May | | |
|---|---|---|
| | WEIGHT (g/fruit) | |
| | 28 March | 15 May |
| AIRES | 23 | 21 |
| CARLSBARD | 25 | 23 |
| CRISTAL | 24 | 22 |

WEIGHT is shown as the average weight per fruit in First Quality Fruits.

FRUIT ANALYSIS

| | ALBION | AIRES | CRISTAL (00.44.194) | CARLSBARD |
|---|---|---|---|---|
| Firmness (KG) | 0.80 | 1.20 | 0.70 | 0.70 |
| Humidity & Volatile Matter (%) | 91.40 | 91.20 | 91.70 | 89.90 |
| Dry Matter (%) | 8.60 | 8.80 | 8.30 | 10.10 |
| PH (to 20°) | 3.20 | 3.20 | 3.40 | 3.40 |
| Acidity as Anhydride Citric (%) | 1.20 | 1.20 | 1.10 | 1.20 |
| Soluble Solids (°Brix) | 6.90 | 6.90 | 6.60 | 8.40 |
| Maturity Index | 5.60 | 5.80 | 6.00 | 7.00 |
| Content in Ascorbic Acid (ppm) | 1122 | 1302 | 1251 | 1330 |
| Dominant Tonality (nm) | 510 | 515 | 510 | 510 |
| Luminosity: | | | | |
| Transmittance to 460 nm | 56.20 | 57.00 | 51.70 | 46.90 |

The following definitions apply:

Firmness: It is the fruit's resistance to penetration measured in Kilograms (Kg). The measure given has been obtained by the penetrometer ROZE Mod. Arbelette, with a 50 $mm^2$ section head.

Dry matter: It is the weight of the residual left from the trituration of the fruit after the drying process at a temperature of 103° C.±2° C. until reaching constant weight.

$$(\%) \text{ Dry Matter} = \frac{\text{Weight Dry Matter}}{\text{Weight Fresh Matter}} \times 100$$

Humidity & volatile matter: Represents the content in volatile matters and water of the fruits.

$$(\%) \text{ Humidity \& Volatile Matter} = 100 - \% \text{ Dry Matter}$$

Maturity index: Relation between Soluble solids and Acidity as Anhydride Citric.

$$\text{Maturity Index} = \frac{\text{Soluble solids}}{\text{Acidity as Anhydride Citric}}$$

The following additional information is provided to further describe the new variety.

Variety: Cristal. Breeder Ref. 00.44.194.

Classification: *Fragaria×ananassa* Duch.

Plant:

*Habit.*—Globose.

*Density.*—Medium.

*Vigor.*—Strong.

*Height.*—About 21 cm.

*Width.*—About 22 cm.

Leaf:

*Upperside.*—RHS green group color (near 141 B to 141 A); underside. — RHS green group color (near 138 B to 138 A).

*Length.*—About 9 cm.

*Width.*—About 12 cm.

*Cross section.*—Slightly concave.

*Leaf surface ondulation or blistering.*—Medium.

*Number of leaflets.*—Three only.

Leaf stem characteristics:

*Color.*—RHS green group (near 139 D).

*Position of hairs.*—Upwards.

*Length.*—About 11 cm.

Terminal leaflet:

*Length/width ratio.*—As long as broad.

*Length.*—About 8.5 cm.

*Width.*—About 8.5 cm.

*Shape of base.*—Obtuse.

*Shape of teeth.*—Crenate.

Petiole:

*Position of hairs.*—Upwards.

*Length.*—About 11 cm.

Stipule:

*Anthocyanin coloration.*—Absent or very weak. Color. — RHS green group coloration (near 139 D).

Stolons:

*Number.*—Few, about 6 to 7.

*Thickness.*—Medium, about 3.1 mm.

*Pubescence.*—Medium.

*Color.*—RHS green group (near 139 D to 143 D).

Inflorescence: Position relative to foliage. — Above.

Flower:

*Size.*—Medium.

*Size of calyx relative to corolla.*—Same size.

*Spacing of petals.*—Overlapping.

Flower characteristics:

*Diameter primary flowers.*—About 2.0–2.5 cm.

*Diameter secondary flowers.*—About 2.0 cm.

*Number of petals.*—Normally about 5. No significant fragrance.

*Time from bloom to mature fruit* (*in Huelva, Spain*).—About 35 to 38 days.

*Staments.*—Numerous with pollen present, fertile and abundant. Length — approximately 4 mm. Color — RHS white group (near 155 D to 155 C).

*Anthers.*—Generally average in size. Color — RHS yellow group (near 12 B to 13 B) and darkening with advanced maturity.

*Pollen.*—Fertile and abundant. Color — RHS yellow orange group (near 14B to 15B).

*Pistils.*—Numerous, generally average in size. Color — RHS yellow group (near 12B to 13C).

Petal:

*Length/width ratio.*—Broader than long.

Fruiting truss:

*Attitude.*—Semi-erect.

Fruit:

*Ratio of length/maximum width.*—Much longer than broad.

*Color.*—RHS red group (near 46 B to 45 A).

*Peduncle length of inflorescence stem.*—Primary fruit about 9 to 11 cm, secondary fruit about 6 to 7 cm, color near 139 D.

Primary fruit:

*Length.*—About 5.5–6.0 cm.

*Width.*—About 3.5–4.0 cm.

Secondary fruit:

*Length.*—About 5.0–5.5 cm.

*Width.*—About 3.0–3.5 cm.

*Size.*—Large.

*Predominant shape.*—Almost cylindrical.

*Difference in shapes between primary and secondary fruits.*—Slight.

*Band without achenes.*—Narrow.

*Color of achenes.*—RHS orange red group (near 33 B to 33 A).

*Unevenness of surface.*—Weak.

*Evenness of color.*—Even.

*Glossiness.*—Strong.

*Insertion of achenes.*—Below surface.

*Insertion of calyx.*—Set above fruit.

*Pose of the calyx segments.*—Reflexed.

*Size of calyx in relation to fruit diameter.*—Slightly smaller.

*Adherence of calyx.*—Strong.

*Firmness.*—Firm.

*Color of flesh.*—RHS red group (near 43 B to 43 A), lightening toward center.

*Distribution of red color of flesh.*—Marginal and central.

*Hollow center.*—Absent or very weakly expressed.

*Sweetness.*—Medium.

*Acidity.*—Medium.

*Time of flowering* (*50% of plants at first flower*).—Early.

*Time of ripening* (*50% of plants with ripe fruits*).—Early.

*Type of bearing.*—Fully remontant (non-flowering runners).

*Chilling.*—Weak.

*Planting date.*—Oct. 15, 2007.

*10% Flowering.*—Nov. 10, 2007.

*First mature fruits.*—Dec. 20, 2007.

*Maturity* (*15–20 gms/plant*).—Jan. 12, 2008.

Time of flowering data: Date of planting: Oct. 15, 2007 in the farm of La Mogalla, in Cartaya (Huelva), Spain, about 7° W., 37° N., 45 feet elevation. 10% flowering occurs about Nov. 10, 2007 with first mature fruit about Dec. 20, 2007 and maturity (15–20 g/plant) about Jan. 12, 2008.

Time of flowers (50% of plants at first flower): About Nov. 17, 2007.

Storage qualities: 'Cristal' fruit maintain their quality characteristics when keeping them in a frigo chamber at temperatures of about 2° C. during 48 hours. The fruit's color remains substantially the same.

Time of ripening: After planting as aforesaid, plants are grown in raised beds undertunnel (small tunnel with small holes in plastic walls). Water and fertilizer were applied through drip irrigation. Time of ripening (50% of plants with ripe fruit) is about Dec. 27, 2007. First mature fruit is about Dec. 20, 2007 and maturity (15–20 gms/plant) is about Jan. 12, 2008.

General: The growing period in Huelva, Spain, where the observations were made, is between about December, 15 and May, 30 of each year, with a maximum production at about mid-April. 'Cristal' is a short variety that benefits from induction to flowering by chilling, usually a few hours are sufficient, preferably at temperatures of 7° C. or less. Normally, the minimum number of hours is accumulated in the field during several days.

Disease resistance: No particular sensitivity to any disease or parasite has been observed for 'Cristal'.

I claim:

1. A new and distinct strawberry plant of the variety substantially as shown and described.

* * * * *